US010278611B2

(12) United States Patent
Sugiura

(10) Patent No.: US 10,278,611 B2
(45) Date of Patent: May 7, 2019

(54) MEDICAL IMAGE DIAGNOSTIC APPARATUS AND MEDICAL IMAGE DISPLAY APPARATUS FOR VOLUME IMAGE CORRELATIONS

(75) Inventor: Satoshi Sugiura, Otawara (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 0 days.

(21) Appl. No.: 13/006,764

(22) Filed: Jan. 14, 2011

(65) Prior Publication Data

US 2011/0172516 A1     Jul. 14, 2011

(30) Foreign Application Priority Data

Jan. 14, 2010   (JP) ................................ 2010-005882

(51) Int. Cl.
| | |
|---|---|
| *A61B 5/055* | (2006.01) |
| *A61B 6/00* | (2006.01) |
| *A61B 6/03* | (2006.01) |
| *A61B 5/00* | (2006.01) |

(52) U.S. Cl.
CPC ............ *A61B 5/055* (2013.01); *A61B 6/5247* (2013.01); *A61B 5/7425* (2013.01); *A61B 6/03* (2013.01); *A61B 6/463* (2013.01); *A61B 6/469* (2013.01); *A61B 6/5223* (2013.01)

(58) Field of Classification Search
CPC ......... A61B 5/055; A61B 5/7425; A61B 6/03; A61B 6/463; A61B 6/469; A61B 6/5223; A61B 5/743
USPC ...................................................... 600/407
See application file for complete search history.

(56) References Cited

U.S. PATENT DOCUMENTS

| | | | | | |
|---|---|---|---|---|---|
| 5,521,720 | A | * | 5/1996 | Yoshida | .................... G06T 3/40 358/296 |
| 5,734,384 | A | * | 3/1998 | Yanof | ..................... G06T 17/10 345/419 |
| 2002/0188193 | A1 | * | 12/2002 | Biglieri et al. | ............... 600/411 |
| 2006/0093199 | A1 | * | 5/2006 | Fram | ..................... A61B 6/5223 382/128 |
| 2006/0267977 | A1 | * | 11/2006 | Barfuss | .................. A61B 6/466 345/419 |
| 2008/0130972 | A1 | * | 6/2008 | Miller | ................... G06F 19/321 382/131 |

(Continued)

FOREIGN PATENT DOCUMENTS

| | | |
|---|---|---|
| JP | 2000-185036 | 7/2000 |
| JP | 2007-282656 | 11/2007 |

(Continued)

OTHER PUBLICATIONS

Lecouvet et al. Clinical Evaluation of Automated Scan Prescription of Knee MR Images, Journal of Magnetic Resonance Imaging 29:141-145, 2009.*

(Continued)

*Primary Examiner* — Serkan Akar
(74) *Attorney, Agent, or Firm* — Nixon & Vanderhye P.C.

(57) ABSTRACT

A medical image diagnostic apparatus has an imaging unit that images volume data of a region-of-interest of an object, an extracting unit that extracts a characteristic point from the volume data; and, a generating unit that generates an observation sectional image from the volume data using the characteristic point and correlation parameters.

8 Claims, 10 Drawing Sheets

(56) References Cited

U.S. PATENT DOCUMENTS

| | | | | |
|---|---|---|---|---|
| 2008/0177172 A1* | 7/2008 | John | ............... | A61B 19/52 |
| | | | | 600/413 |
| 2009/0012390 A1* | 1/2009 | Pescatore et al. | ............ | 600/425 |
| 2010/0049036 A1* | 2/2010 | Kimh | ................. | A61B 6/5247 |
| | | | | 600/425 |

FOREIGN PATENT DOCUMENTS

| JP | 2008-188193 | 8/2008 |
|---|---|---|
| JP | 2009-022368 | 2/2009 |

OTHER PUBLICATIONS

Young et al., Automated planning of MRI neuro scans, Medical Imaging 2006: Image Processing, SPIE vol. 6144, 61441M, 2006.*
S. Young et al., "Robust Anatomy Recognition for Automated MR Neuro Scan Planning"; Proc. Intl. Soc. Mag. Reson. Med. 14. (2006) : 1588.

* cited by examiner

MEDICAL IMAGE DIAGNOSTIC APPARATUS AND MEDICAL IMAGE DISPLAY APPARATUS FOR VOLUME IMAGE CORRELATIONS

CROSS-REFERENCE TO RELATED APPLICATIONS

This application is based upon and claims the benefit of priority from Japanese Patient application No. 2010-005882, filed on Jan. 14, 2010, the entire contents of each of which are incorporated herein by reference.

TECHNICAL FIELD

Embodiments described herein relate generally to medical diagnostic techniques for imaging the inside of an object and forming an image of the inside of the object, and, more particularly to a medical image diagnostic apparatus that executes the imaging process and a medical image display apparatus that displays the image.

BACKGROUND

Medical image diagnostic apparatuses such as an MRI apparatus and an X-ray CT apparatus are widely applied to clinical applications because a lot of medical knowledge can be obtained from volume data of a three-dimensional space collected from a region-of-interest (ROI) of an object. In three-dimensional imaging in which such volume data is obtained, data of all the region-of-interest can be obtained by once performing an imaging process. A two-dimensional image of an arbitrary section can be obtained by data processing after the imaging process.

Therefore, it is unnecessary to accurately perform positioning of the object in the imaging process. For an operator, substantial total hours spent at work excluding data processing time is, therefore, reduced. Moreover, detailed anatomical knowledge concerning the region-of-interest is unnecessary. In other words, it is unnecessary to perform imaging again in order to reacquire a sectional image (a two-dimensional image) of the object to be observed. This is extremely convenient from the viewpoints of accuracy and promptness of medical diagnosis.

However, when an imaging result is read, since a two-dimensional image is used, a long time is consumed for data processing for generating, from collected volume data, a two-dimensional image to be observed. This hinders further improvement of accuracy and promptness of medical diagnosis.

A related art for solving such a problem discloses a method of displaying, in a medical image observation supporting system established on a network, the same section with respect to a new test image on the basis of position information of test images in the past with an apparatus coordinate system set as a reference (e.g., Japanese Patent Laid-Open No. 2009-22368).

Another related art discloses a method of applying, in a medical image display apparatus, on the basis of incidental information (sectional position information and sectional direction information) of certain image data, MPR (multiplanar reconstruction) processing for the same section to other image data by performing drag and drop operation between image display areas (e.g., Japanese Patent Laid-Open No. 2007-282656).

In both the related arts, accuracy of a sectional position is assured on condition that there are images obtained by imaging the same patient in the same modality in the past. Further, even if the condition is satisfied, unless a positional relation between a patient and an apparatus is fixed, it is difficult to reproduce the same section.

Specifically, for example, when head imaging is performed by MRI, in performing positioning with a projector, operation for designating completely the same position as that in the past and setting a specific region of a patient in the center of an apparatus is requested. Further, it is requested that tilts of the head of the patient are the same in all directions between imaging in the past and imaging at the present. These requests are unrealistic.

BRIEF SUMMARY

It has been devised in view of such circumstances and object to provide a medical image diagnostic apparatus and a medical image display apparatus that find, in a coordinate system in an imaged three-dimensional image rather than of an apparatus coordinate system, a reference used for generating a sectional image (a two-dimensional image).

Accordingly the medical image diagnostic apparatus and a medical image display apparatus are provided with which, if correlation parameters are calculated in advance, a sectional image necessary for reading is automatically formed simply by performing imaging of volume data and accurate and prompt diagnosis is possible.

DETAILED DESCRIPTION

MRI apparatus 10 is explained below as an example of an embodiment of a medical image diagnostic apparatus on the basis of the accompanying drawings.

Figure 1:
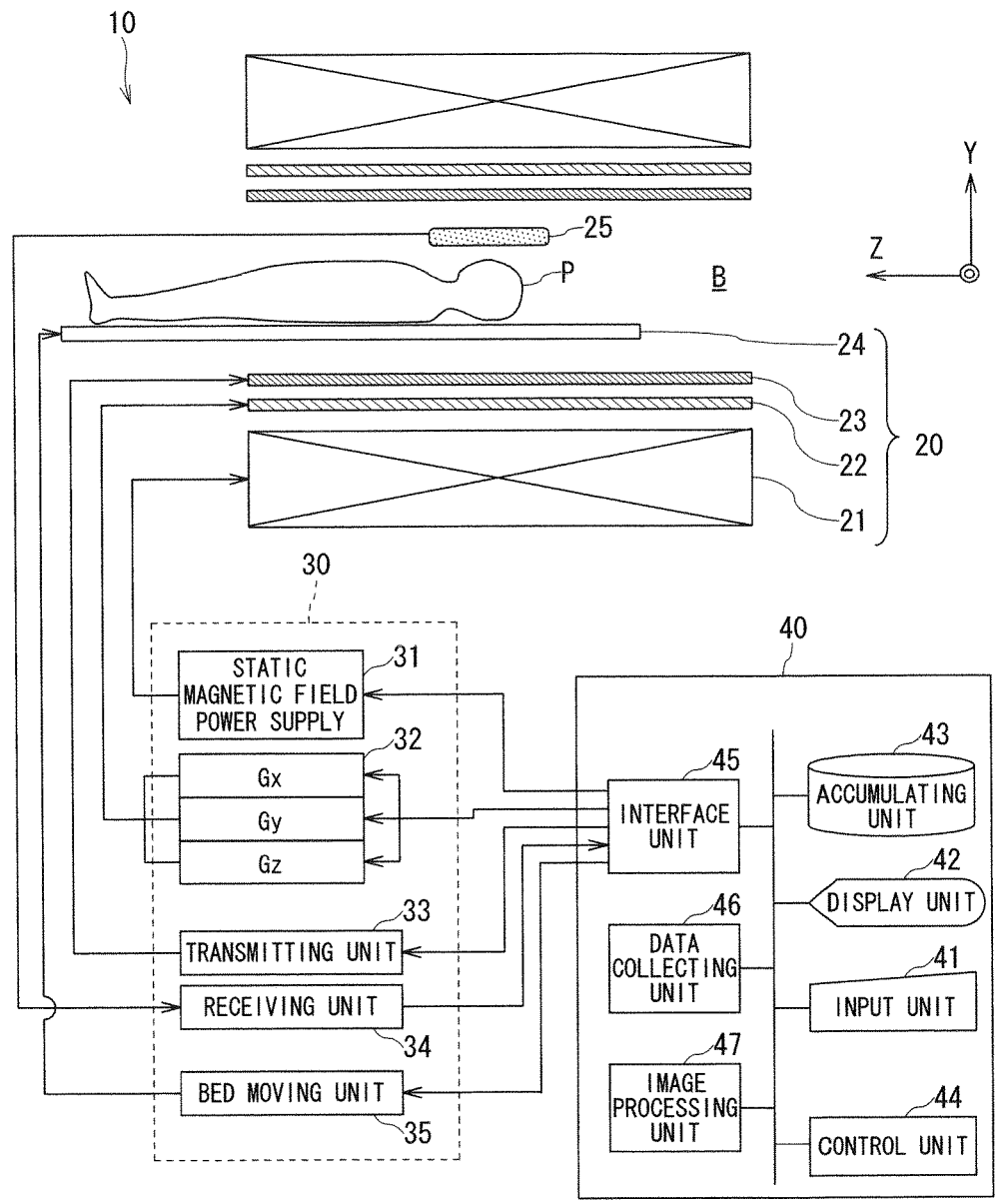
FIG. 1 is a block diagram showing an embodiment of a medical image diagnostic apparatus.

As shown in FIG. 1, the MRI apparatus 10 includes an imaging unit 20 that applies a controlled magnetic field to a region-of-interest of an object P and irradiates an RF wave, a receiving coil 25 that receives a response wave (an NMR (nuclear magnetic resonance) signal) from the object P and outputs an analog signal, a driving unit 30 that controls the magnetic field applied to the object P and controls transmission and reception of the RF wave, and a data operating unit 40 that sets a control sequence for the driving unit 30 and processes various data signals to generate an image.

The center axis of a cylindrical bore B in which the object P is placed is set as a Z axis. An X axis is defined in the horizontal direction orthogonal to the Z axis and a Y axis is defined in the vertical direction orthogonal to the Z axis.

The MRI apparatus 10 is configured as explained above. Therefore, a nuclear spin of an atomic nucleus forming the object P is oriented in a magnetic field direction (the Z axis) and performs precession at a Larmor frequency peculiar to the atomic nucleus with the magnetic field direction set as an axis.

When an RF pulse having a frequency the same as the Larmor frequency is irradiated, an atom develops a nuclear magnetic resonance (NMR) phenomenon in which the atom resonates, absorbs energy, and is excited. After the NMR phenomenon is developed, when the RF pulse irradiation is stopped, the atom outputs an electromagnetic wave (an NMR signal) having a frequency same as the Larmor frequency in a relaxation process in which the atom discharges energy and returns to an original steady state.

The output NMR signal is received by the receiving coil 25 as a response wave from the object P. The region-of-interest of the object P is converted into an image in the data operating unit 40.

The imaging unit 20 includes a static magnetic field generating unit 21, a gradient magnetic field generating unit 22, an RF irradiating unit 23, and a bed 24 for placing the object P in the bore B.

The driving unit 30 includes a static magnetic field power supply 31, a gradient magnetic field power supply 32, a transmitting unit 33, a receiving unit 34, and a bed moving unit 35 that moves the bed 24 to an arbitrary position in the Z axis direction.

The data operating unit 40 includes an input unit 41 that receives various kinds of operations and information input from an operator (not shown), a display unit 42 that screen-displays various images and various kinds of information concerning the region-of-interest of the object P, an accumulating unit 43 that stores computer programs for executing various kinds of processing, control parameters (correlation parameters, etc.), image data (a three-dimensional model image, etc.), and other electronic data, a control unit 44 that generates a control sequence for driving the driving unit 30 and collectively controls the operations of the other functional units, an interface unit 45 that executes transmission and reception of various signals between the data operating unit 40 and the driving unit 30, a data collecting unit 46 that collects volume data including a group of NMR signals deriving from the region-of-interest, and an image processing unit 47 that forms an observation sectional image on the basis of the volume data.

The data operating unit 40 is a computer that causes the functional units to operate. The data operating unit 40 may cause the functional units to perform a designated calculation, data processing, and generation of a control sequence on the basis of computer programs installed in the accumulating unit 43.

In the input unit 41, setting of imaging conditions for the imaging unit 20 is performed to prevent the resolution of an observation sectional image from changing depending on a sectional direction.

The static magnetic field generating unit 21 uses electric current, which is supplied from the static magnetic field power supply 31, to a spiral coil wound around the Z axis and causes the spiral coil to generate an induction magnetic field and generate a static magnetic field in the Z axis direction in the bore B. The region-of-interest of the object P is set in an area in which uniformity of the static magnetic field formed in the bore B is high.

The gradient magnetic field generating unit 22 includes an X coil, a Y coil, and a Z coil not shown in the figure. The gradient magnetic field generating unit 22 is provided on the inner circumferential surface of the static magnetic field generating unit 21 formed in a cylindrical shape.

The X coil, the Y coil, and the Z coil superimpose, while respectively switching the X axis direction, the Y axis direction, and the Z axis direction in order, a gradient magnetic field on the uniform magnetic field in the bore B and give an intensity gradient to the static magnetic field.

The switching of the gradient magnetic field to be superimposed is realized by different pulse signals being respectively output to the X coil, the Y coil, and the Z coil according to the control sequence. Consequently, the position of the object P where the NMR phenomenon is developed can be specified. Position information on a three-dimensional coordinate necessary for forming an image of the object P is given.

The RF irradiating unit 23 is incorporated in the imaging unit 20 shown in FIG. 1. However, in some cases, the RF irradiating unit 23 is provided in the bed 24 or integrated with the receiving coil 25.

The RF irradiating unit 23 is incorporated in the imaging unit 20 shown in FIG. 1. However, in some case, the RF irradiating unit 23 is provided in the bed 24 or integrated with the receiving coil 25.

The receiving coil 25 detects a response wave (an NMR signal) from the object P. The receiving coil 25 is arranged near the object P in order to detect the NMR signal with high sensitivity.

In the receiving coil 25, when an electromagnetic wave of the NMR signal crosses an element wire of the receiving coil 25, a feeble current is generated on the basis of electromagnetic induction. In the receiving unit 34, the feeble current is amplified by an amplifier (not shown), converted from an analog signal into a digital signal, and sent to the data operating unit 40.

Figure 2:
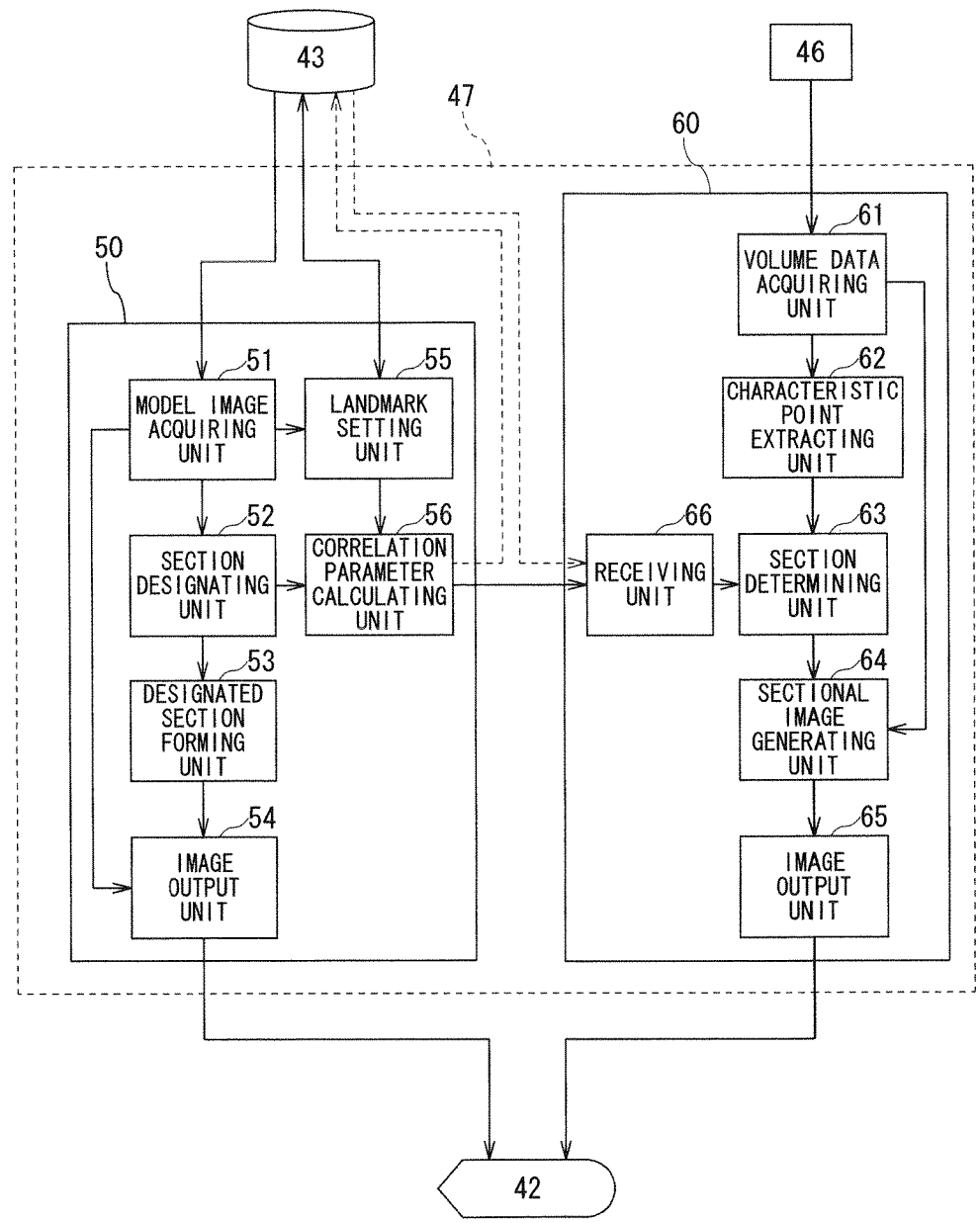
FIG. 2 is a block diagram showing details of an image processing unit applied to the embodiment.

As shown in FIG. 2, the image processing unit 47 designates, in a condition setting unit 50, a section (a designated section) to be observed using a three-dimensional model image included in a database established in the accumulating unit 43. The image processing unit 47 forms, in a diagnostic image forming unit 60, an observation sectional image of the object P (FIG. 1) corresponding to the designated section on the basis of the volume data collected by the data collecting unit 46.

In this embodiment, a sectional image of the head is illustrated as the sectional image of the object P to be processed by the image processing unit 47. However, for example, the spine, the joint, the heart, the blood vessel, or other regions can also be set as a target of the processing.

The condition setting unit 50 includes a model image acquiring unit 51, a section designating unit 52, a designated section forming unit 53, an image output unit 54, a landmark setting unit 55, and a correlation parameter calculating unit 56.

Figure 3:
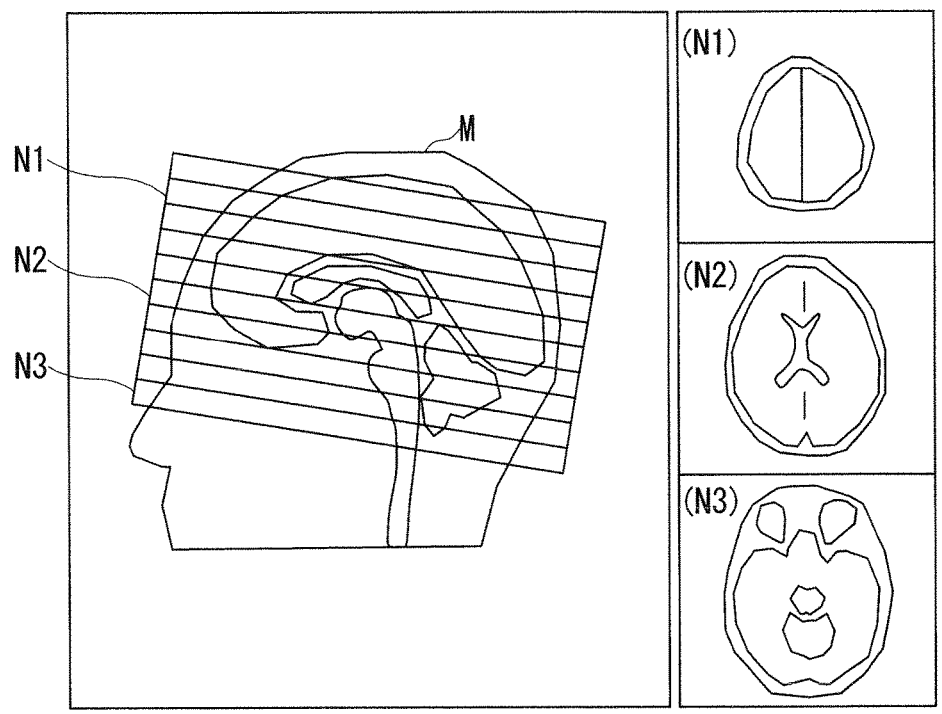
FIG. 3 is a diagram of a screen on which a three-dimensional model image and designated sections designated as observation sections applied to the embodiment are displayed.

As shown in FIG. 3, the condition setting unit 50 configured in this way causes the display unit 42 to display a three-dimensional model image M invoked from the accumulating unit 43 (FIG. 2) and to display, in multiple stages, rectangles indicating the positions and the thicknesses of designated sections N according to the operation of the input unit 41.

The designated sections N corresponding to the respective rectangles are displayed in slices such as N1 to N3. It is possible to check what kinds of images the designated sections N are. As the designated sections N in FIG. 3, only three designated sections N1 to N3 are selectively shown. However, the designated sections N are present by a number equivalent to the rectangles displayed in multiple stages.

Figure 4:
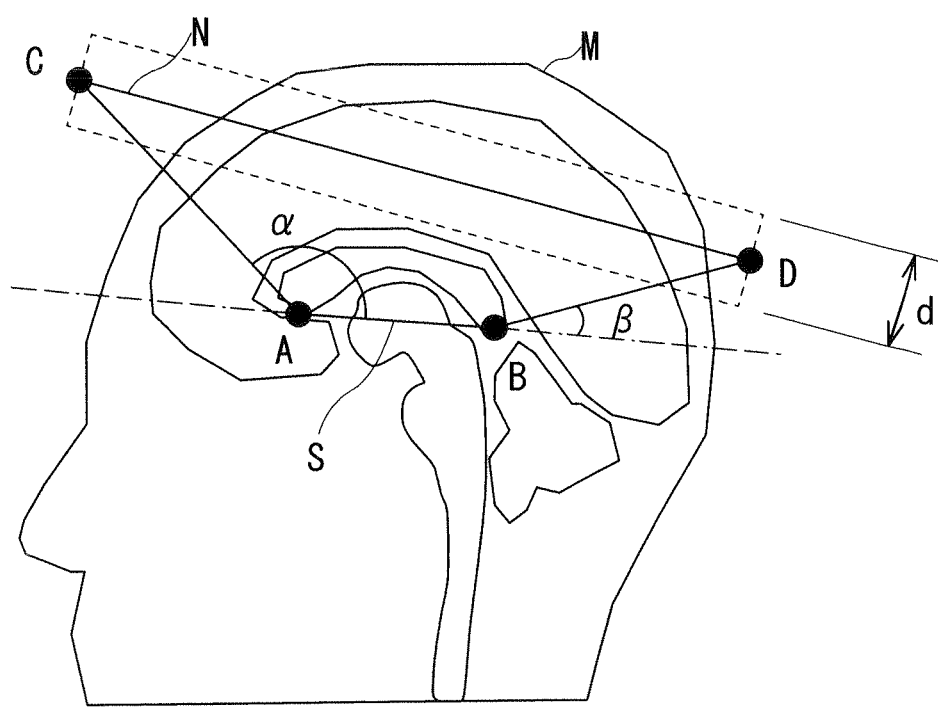
FIG. 4 is an explanatory diagram of a method of calculating correlation parameters applied to the embodiment.

Further, as shown in FIG. 4, the condition setting unit 50 calculates correlation parameters between the designated section N and a landmark S.

The model image acquiring unit 51 (FIG. 2) selects, according to the operation of the input unit 41 (FIG. 1) by an operator such as a physician or a technician, a three-dimensional model image corresponding to the region-of-interest of the object P (FIG. 1) from the database established in the accumulating unit 43. The selected three-dimensional model image is displayed on the display unit 42 by the image output unit 54 as indicated by sign M in FIG. 3.

The three-dimensional model image M is a virtual image of a human body structure artificially created on the basis of numerical value data or an image reformed from volume data imaged by a modality such as an MRI apparatus. In other words, the three-dimensional model image M only has to be a three-dimensional image with which it is possible to cause the display unit 42 to display a tissue structure of an arbitrary section designated in a standard human body 2 and check the tissue structure.

When the image imaged by the modality is used as the three-dimensional model image M, images imaged by the same modality or different modalities that image the volume data processed by the diagnostic image forming unit 60 can also be applied.

As illustrated as position determination for an observation section in the head in FIG. 3, the section designating unit 52 designates, according to the operation of the input unit 41 (FIG. 1), the positions and the thicknesses of the designated sections N in the three-dimensional model image M, which is a head median plane image, as lines that section the region-of-interest.

The designated section forming unit 53 forms two-dimensional images of organism tissues of the designated sections N (N1, N2, and N3), the positions of which are designated by the section designating unit 52.

Formed slice groups of the designated sections N (N1, N2, and N3) are previewed by the image output unit 54 as shown in the right column in FIG. 3.

In the illustration, a sectional area having a section by a ruled line displayed in a median section of the head in FIG. 4 as thickness and extending in a direction orthogonal to the screen is designated as the designated section N. When plural slice groups are designated as shown in the figure, plural designated sections N are designated.

The designated sections N correspond to the sectional images (observation sectional images) of the volume data imaged by the imaging unit 20. And the sectional images are finally observed.

The designated sections N to be designated are not limited to the sections in the direction shown in the figure. Sections in an arbitrary coordinate surface in the three-dimensional model image M can be designated by the input unit 41.

The landmark setting unit 55 sets a landmark in the three-dimensional model image M.

The landmark of the three-dimensional model image M indicates an anatomical characteristic point in the volume data or a luminance characteristic point on display in the display unit 42.

In the illustration of FIG. 4, a segment AB connecting lower parts of the corpus callosum on the head median section as an anatomical landmark S is extracted. However, the landmark S is not limited to this and may be any landmark as long as the landmark corresponds to a characteristic point extracted from the volume data in the diagnostic image forming unit 60 such as the radix nosi portion, the corpus ponotulbare and portions following the corpus ponotulbare, the anterior commissure, the posterior commissure, or the ventricle contour.

As the landmark S of the three-dimensional model image M, a landmark registered to correspond to the three-dimensional model image M without undergoing a process for directly extracting the landmark from the three-dimensional model image M may be stored in the accumulating unit 43.

The correlation parameter calculating unit 56 calculates correlation parameters concerning the positions of the landmark S of the three-dimensional model image M and the designated section N as shown in FIG. 4.

As a specific example, as shown in FIG. 4, the landmark S identified by the landmark setting unit 55 (FIG. 2) and the designated section N designated from the section designating unit 52 are specified. In this case, a positional relation between the landmark S and the designated section N is specified by a segment |AB|, a segment |CD|, a segment connecting both ends of the segment |AB| and the segment |CD|, and an angle $\alpha$ and an angle $\beta$ formed by these segments. Numerical values of the segments and the angles are stored in the accumulating unit 43 as correlation parameters together with thickness d.

If the position of a characteristic point of volume data corresponding to the landmark S of the three-dimensional model image M is determined according to the correlation parameters, formation of an observation sectional image of volume data corresponding to the designated section N of the three-dimensional model image M can always be reproduced in the same position. The correlation parameters are not limited to the variables illustrated above and may be any correlation parameters according to which a relative positional relation between the landmark S and the designated section N can be reproduced.

The calculated correlation parameters are stored in the accumulating unit 43 in association with character data such as names or numbers related to medical information such as positioning information, imaging regions, test content, and disease names and thereafter can be repeatedly used.

For example, as the positioning information, the correlation parameters are stored together with names such as "brain screening", "inner ear", "glandula pituitaria", and "acute cerebral infarction" in the case of the head, "left ventricle brachyaxis" and "four-cavity section" in the case of the heart, and "C2 to C7 disks" in the case of the spine.

Consequently, when a typical test is performed plural times or the same test is applied to different patients, a person requesting the test only has to designate a name such as a test name and invoke the correlation parameters corresponding to the name from the accumulating unit 43. In other words, in such a routine test, it is unnecessary to perform, every time the test is performed, the operation for designating the designated section N from the three-dimensional model image M. It is unnecessary to cause the condition setting unit 50 to function in the image processing unit 47.

The diagnostic image forming unit 60 includes a volume data acquiring unit 61, a characteristic point extracting unit 62, a section determining unit 63, a sectional image generating unit 64, an image output unit 65, and a receiving unit 66.

The diagnostic image forming unit 60 configured in this way acquires the volume data of the region-of-interest of the object P imaged by the imaging unit 20 of the MRI apparatus, generates an observation sectional image in a plane position corresponding to the designated section N set by the condition setting unit 50, and causes the display unit 42 to display the observation sectional image.

The volume data is representatively obtained by an imaging method including two-dimensional phase encode and one-dimensional frequency encode orthogonal to each other. However, some other volume data is obtained by sweeping an arbitrary three-dimensional trajectory or includes plural two-dimensional multiple slices.

In a method of reforming a two-dimensional observation image from such volume data, processing such as Fourier transformation is executed on the volume data.

Depending on an image type of MRI, the following characteristic point extracting unit 62 cannot accurately extract a characteristic point. A characteristic point cannot be accurately extracted in the case of an image obtained by special imaging such as an imaging method with relatively low spatial resolution and inter-tissue contrast as in a diffusion-weighed image or an imaging method with which only blood vessels are highlighted and extracted as in MR angiography.

A method of forming an observation sectional image from volume data acquired by such special imaging is mentioned. Acquire the volume data with contrast of the characteristic point being higher than other tissues. It is easy for automatic extraction of an anatomical characteristic point.

The volume data acquired by the special imaging and the volume data for characteristic point extraction explained above need to be continuously imaged by the imaging unit 20 without moving the object P.

The volume data for characteristic point extraction imaged in this way is sent to the characteristic point extracting unit 62. The volume data acquired by the special imaging is sent to the sectional image generating unit 64.

The characteristic point extracting unit 62 extracts a characteristic point in the volume data (imaged by the MRI apparatus 10) corresponding to the landmark identified by the three-dimensional model image M (the processing in the condition setting unit 50).

In this embodiment, since the condition setting unit 50 identifies the two points A and B of the lower parts of the corpus callosum in the head median section as landmarks, the characteristic point extracting unit 62 extracts, as characteristic points, corresponding two points of the lower parts of the corpus callosum in the head median section from the volume data.

A publicly-known technique is adopted to extract such characteristic points from the volume data. Examples of a specific method of detecting, on an image, an anatomical characteristic point from a tissue contrast and a standard human body structure include Non-Patent Document "Robust anatomy recognition for automated MR neuro scan planning" Young S. et al. Proc. Intl. Soc. Mag. Reson. Med. 14 (2006): 1588.

The section determining unit 63 determines, according to a relation between the characteristic points extracted by the characteristic point extracting unit 62 and the correlation parameters received by the receiving unit 66, position information of the observation sectional image of the volume data corresponding to the designated sections N (see FIG. 3) formed by the condition setting unit 50.

For specific explanation, the characteristic points extracted by the characteristic point extracting unit 62 are represented as a segment A'B' (not shown) and the correlation parameters are represented as angles ($\alpha$, $\beta$) formed by position vectors of points A, B, C, and D and segments connecting these points (FIG. 4).

A ratio of length |A'B'| between the extracted characteristic points and length |AB| in the three-dimensional model image M is calculated. Points C' and D' (not shown) at both ends of a section that should be created on the imaged volume data are determined from the angles $\alpha$ and $\beta$. For example, the point C' can be determined as a point at a distance |A'C'|=|AC|·|A'B'|/|AB| in the direction of the angle $\alpha$ with respect to the segment A'B' from the point A'.

The sectional position is determined by using reference in a coordinate system in an imaged three-dimensional image rather than in an apparatus coordinate system. Thus, it is possible to accurately set correspondence between the observation sectional image of the volume data and the designated section N designated by the three-dimensional model image M.

The sectional image generating unit 64 generates an observation sectional image from the volume data on the basis of the position information determined by the section determining unit 63 and outputs the observation sectional image to the display unit 42 through the image output unit 65.

Specifically, the sectional image generating unit 64 generates a two-dimensional image by applying image forming processing such as Fourier transformation to data of the thickness d in a section including the points C' and D' and perpendicular to the median section among data of the volume data obtained by the volume data acquiring unit 61.

Consequently, the sectional image generating unit 64 reproduces, on the imaged volume data, a section equivalent to the section defined in the segment CD in the three-dimensional model image M by the operation of the condition setting unit 50.

The sectional image generating unit 64 creates nuclear spin spectrum data or a two-dimensional image corresponding to all the slice sections designated by the section designating unit 52 and accumulates the nuclear spin spectrum data or the two-dimensional image in the accumulating unit 43 or causes the display unit 42 to display the nuclear spin spectrum data or the two-dimensional image.

As a method of reconstructing an arbitrary two-dimensional section from the three-dimensionally imaged volume data, besides using the technique of multi-planar reconstruction (MPR) explained above, it is also possible to use a technique for applying post processing such as maximum intensity projection (MIP) to the volume data and automatically generating a target processed image. In the latter case, the operator needs to designate, for example, a projection angle and the number of projections of the maximum intensity projection prior to imaging.

When a target observation sectional image is formed from the volume data acquired by the special imaging, the position information of the section given by the section determining unit 63 is based on the volume data for characteristic point extraction.

Therefore, the sectional image generating unit 64 applies the position image to the volume data for sectional observation by the special imaging acquired from the volume data acquiring unit 61 and generates the target observation sectional image.

On condition that the object P does not move while the volume data for characteristic point extraction and the volume data for sectional observation are continuously imaged, an observation sectional image corresponding to the designated section N designated by the condition setting unit 50 is obtained.

An operation procedure for reforming a target observation sectional image from volume data imaged by a medical image diagnostic apparatus (the MRI apparatus 10) according to an embodiment is explained with reference to a flowchart of FIG. 5 (FIGS. 1 and 2 are referred to as appropriate).

First, an operator acquires, by operating the input unit 41, the three-dimensional model image M corresponding to an imaging target of the object P from the accumulating unit 43 (reference numeral 51 in FIG. 2) and causes the display unit 42 to display the three-dimensional model image M (S11).

The three-dimensional model image M to be displayed is a virtual image or a standard MRI photographed image as explained above.

Simultaneously with the three-dimensional model image M being acquired, setting of a landmark of the three-dimensional model image M (reference numeral 55 in FIG. 2) is performed (S12). As the setting of the landmark, the landmark is directly searched from the three-dimensional model image M or identification data registered in association with the three-dimensional model image M is acquired from the accumulating unit 43.

Subsequently, the operator designates the designated section N (reference sign 52 in FIG. 2) while referring to an image of a sectional tissue of the three-dimensional model image M displayed on the display unit 42 (FIG. 3) (S13).

Simultaneously with the designated section N being designated in this way, correlation parameters concerning a positional relation with the set landmark are calculated (reference numeral 56 in FIG. 2) and stored in the accumulating unit 43 (S14).

The operator sets the object P in the imaging unit 20 of the MRI apparatus and performs imaging (S15). After volume data is acquired (reference numeral 61 in FIG. 2, S16), extraction of characteristic points in the volume data is automatically performed (reference numeral 62 in FIG. 2, S17).

The operator receives correlation parameters calculated by the condition setting unit 50 (or stored in the accumulating unit 43) (reference numeral 66 in FIG. 2), determines, on the basis of the extracted characteristic points, a coordinate of an observation sectional image to be displayed (reference numeral in FIG. 2) and generates a target observation sectional image from the volume data (reference numeral 64 in FIG. 2, S18). The generated observation sectional image is displayed on the display unit 42 and stored in the accumulating unit 43 (S19).

The flow from S11 to S14 and the flow from S15 to S19 are not always continuously executed. In some cases, the flows are separately executed.

When imaging work is standardized, the flow from S11 to S14 is omitted and the flow from S15 to S19 can be executed repeatedly using many times correlation parameters calculated in the past.

When the imaging work is standardized in this way, the operator does not need to know information peculiar to a patient requested for a test, for example, a predicted position of a disease. The operator does not need to have anatomical knowledge. The operator can generate an observation sectional image optimum for medical diagnosis.

An operation procedure for reforming a target observation sectional image from volume data imaged by a medical image diagnostic apparatus (the MRI apparatus 10) according to another embodiment is explained with reference to a flowchart of FIG. 6 (FIGS. 1 and 2 are referred to as appropriate).

Figure 5:
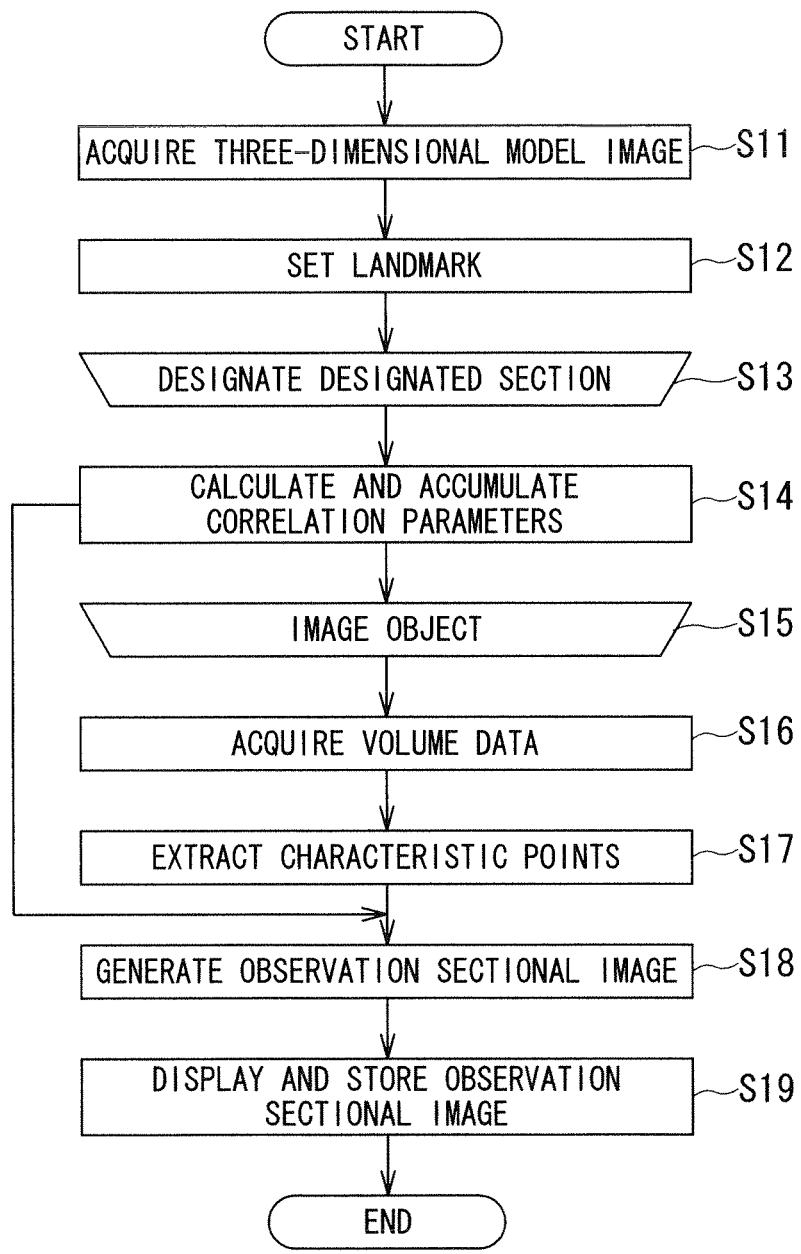
FIG. 5 is a flowchart for explaining the operation of a medical image diagnosis apparatus according to an embodiment.

In the operation flow shown in FIG. 5, it is easy to automatically detect an anatomical characteristic object from the volume data from which the target observation sectional image is obtained. However, in FIG. 6, an observation sectional image is obtained from volume data, in which automatic detection of a characteristic object is difficult, obtained by, for example, a special imaging method with relatively low spatial resolution and inter-tissue contrast as in a diffusion-weighed image or an imaging method with which only blood vessels are highlighted and extracted as in MR angiography.

Figure 6:
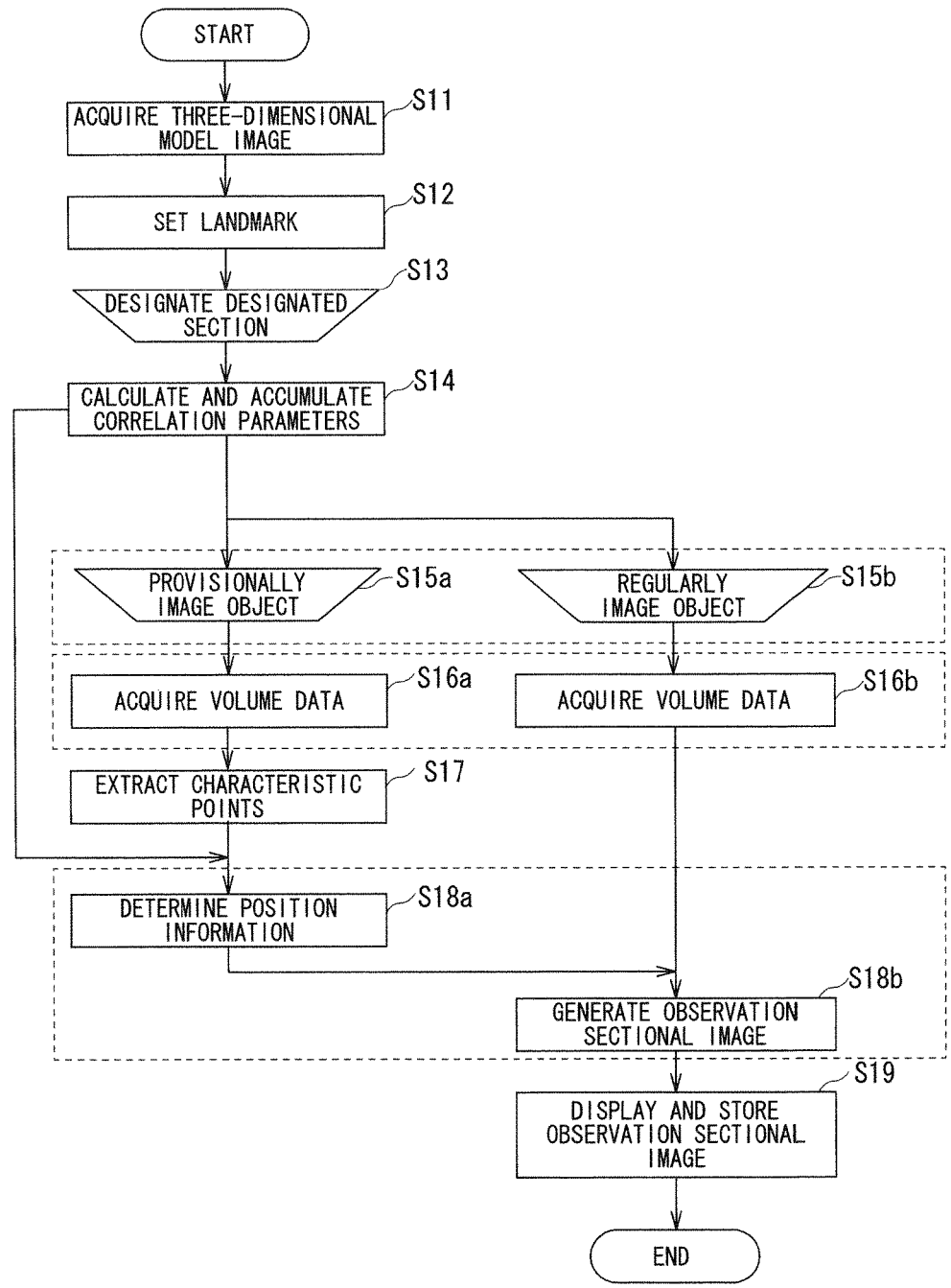
FIG. 6 is a flowchart for explaining the operation of a medical image diagnostic apparatus according to another embodiment.

An operation flow from steps S11 to S14 in FIG. 6 is the same as the corresponding operation flow in FIG. 5. Therefore, the explanation of the operation flow in FIG. 5 is applied and explanation of the steps S11 to S14 is omitted.

The operator sets the object P in the imaging unit 20 of the MRI apparatus and performs provisional imaging of volume data by an imaging method with which automatic extraction of a characteristic object is easy (S15*a*). Subsequently, the operator performs regular imaging of volume data by special imaging (S15*b*). Whichever of the provisional imaging and the regular imaging may be performed first.

The operator acquires volume data for characteristic point extraction from the provisional imaging (S16*a*) and acquires volume data for sectional observation from the regular imaging (S16*b*).

Extraction of characteristic points is automatically performed from the acquired volume data for characteristic point extraction (S17). The operator receives correlation parameters and determines, on the basis of the extracted characteristic points, a coordinate (position information) of an observation sectional image to be displayed (S18*a*).

The operator applies the position information to the acquired volume data for sectional observation (S16*b*), generates an observation sectional image (S18*b*), displays the observation sectional image on the display unit 42, and stores the observation sectional image in the accumulating unit 43 (S19).

A medical image display apparatus according to an embodiment of the present invention is explained with reference to FIG. 7.

A medical image display apparatus 11 according to this embodiment is obtained by independently providing the function of the image processing unit 47 of the medical image diagnostic apparatus 10 shown in FIG. 1.

The medical image display apparatus 11 and the MRI apparatus 12 (the modality) are connected to a common network W via communication units 48 included therein. In this embodiment, the accumulating unit 43 is shared on the network W.

Figure 7:
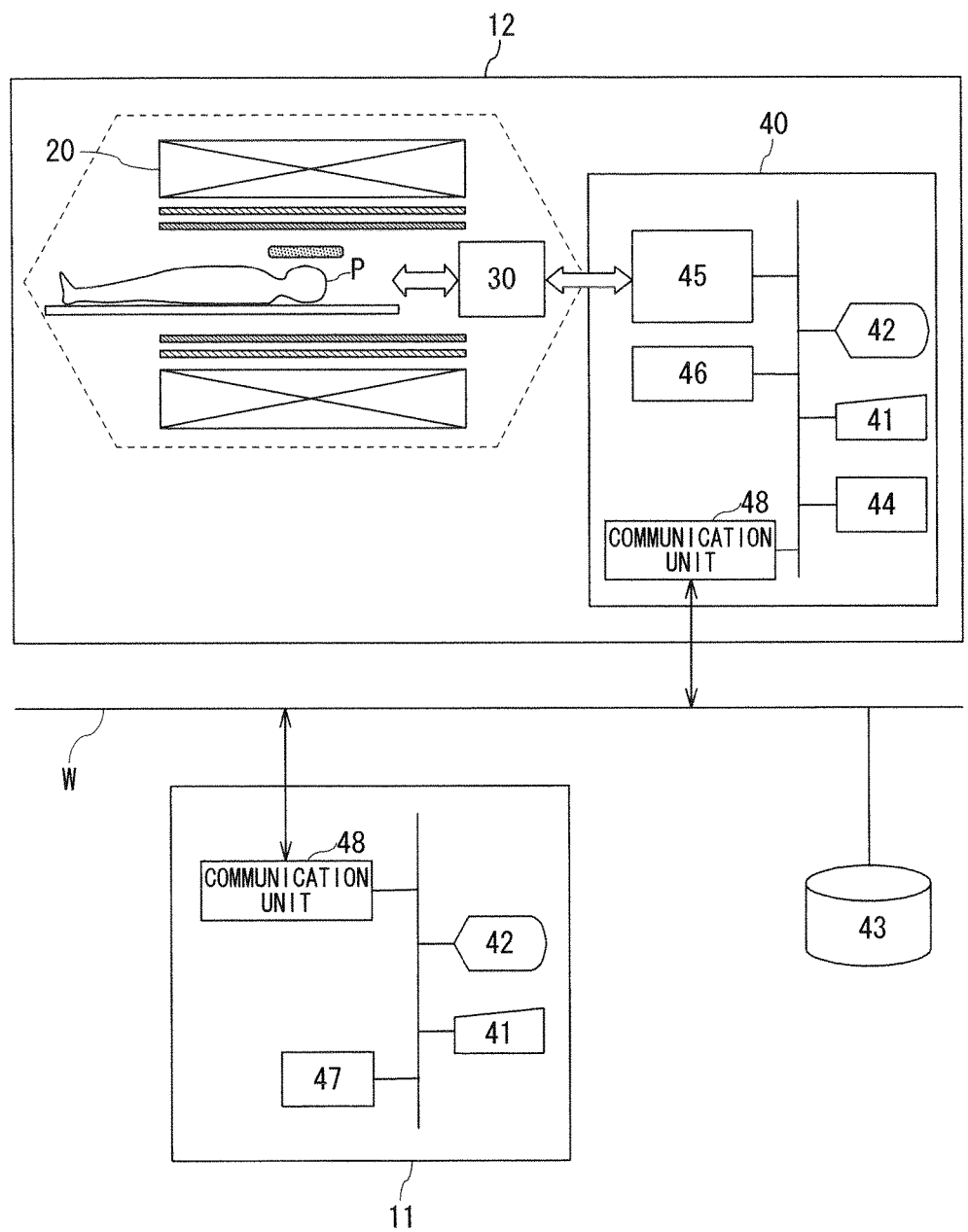
FIG. 7 is a block diagram showing an embodiment of a medical image display apparatus.

Functional units shown in FIG. 7 same as those shown in FIG. 1 are denoted by the same reference numerals and signs, the above explanation is cited, and explanation of the functional units is omitted.

Since the medical image display apparatus 11 is configured in this way, it is possible to carry out the exemplary processes simply by adding, in an information network system in a hospital in which imaging data by various modalities are collectively managed, a new computer separately from the different imaging modalities.

The operation of the medical image display apparatus according to this embodiment is explained with reference to a flowchart of FIG. 8.

Figure 8:
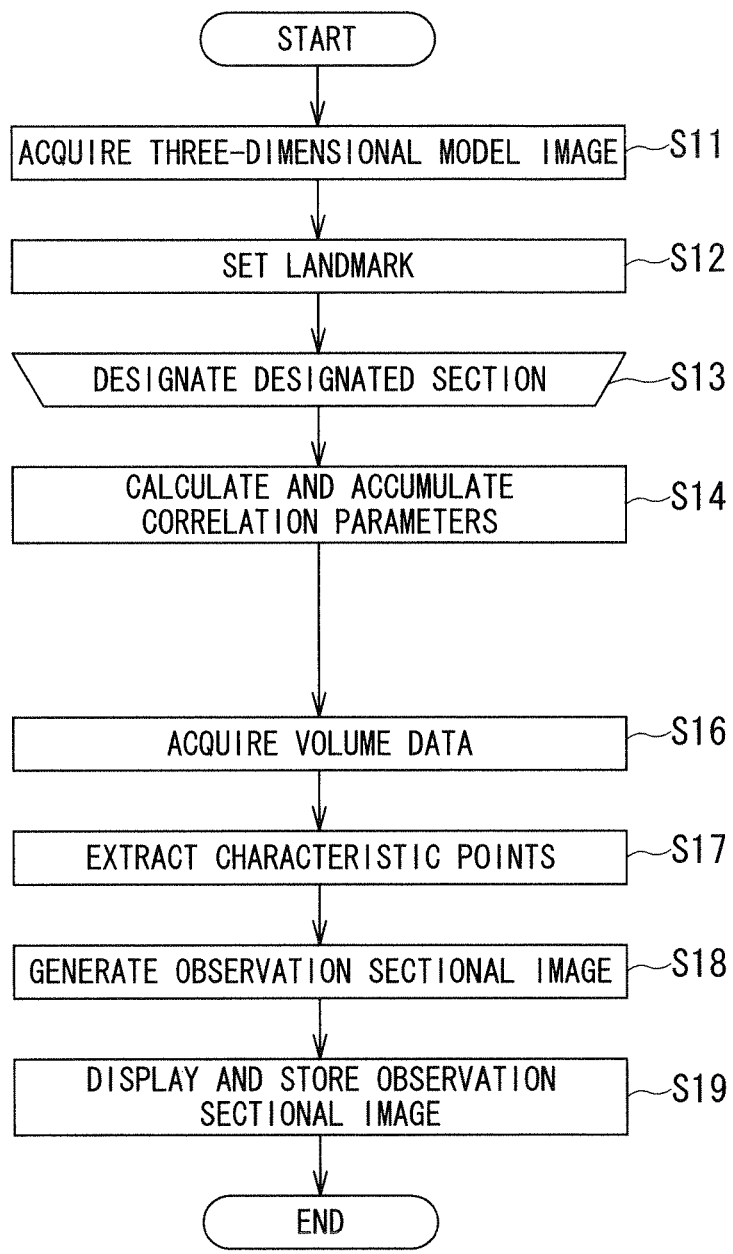
FIG. 8 is a flowchart for explaining the operation of a medical image display apparatus according to an embodiment.

Operation steps shown in FIG. 8 same as those shown in FIG. 5 are denoted by the same reference signs, the above explanation is cited, and explanation of the operation steps is omitted.

In this embodiment, an operator carries out all kinds of work in S11 to S19 by operating the input unit 41 of the medical image display apparatus 11 arranged in a reading room separate from a photographing room in which various modalities such as the MRI apparatus 12 are set.

The operator acquires the three-dimensional model image M (FIG. 3) in a place where the operator cannot directly see the object P, designates the designated section N, and calculates correlation parameters (S11 to S14). Therefore, the operator determines, according to necessity, information concerning positioning from transfer information such as a patient name, a patient number, a date of birth, a gender, patient information such as a physician in charge, and test reservation information.

A step for actually imaging volume data of the object P with the MRI apparatus 12 may be at arbitrary timing as long as the step is performed before S16. The imaged volume data may be stored in the accumulating unit 43 on the network W. The image processing unit 47 directly accesses the accumulating unit 43, acquires the volume data through the network W, generates an observation sectional image according to extraction of characteristic points and application of correlation parameters, and causes the display unit 42 to display the observation sectional image (S16 to S19).

Figure 9:
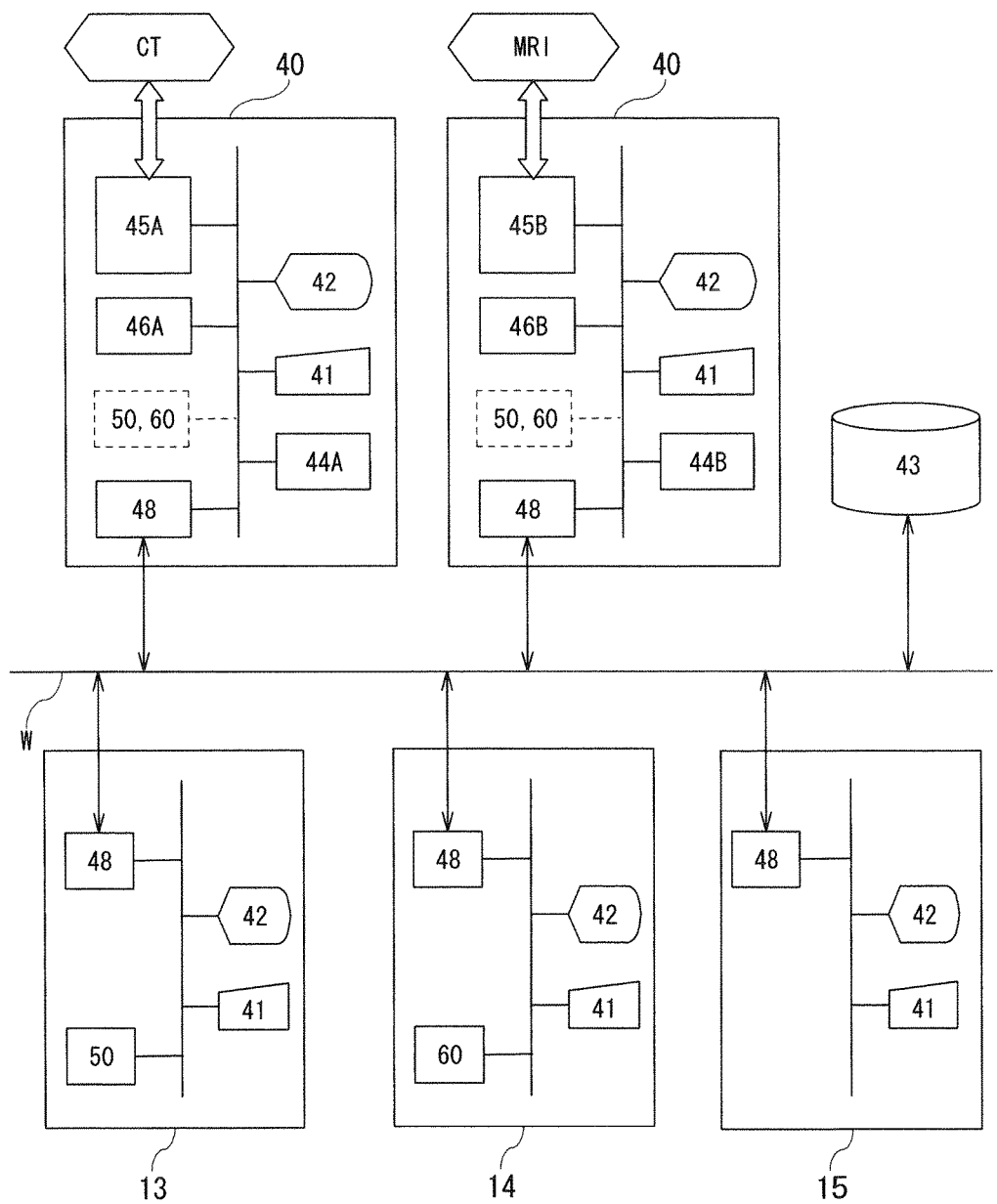
FIG. 9 is a block diagram showing the medical image diagnostic apparatus and the medical image display apparatus according to another embodiment.

A medical image diagnostic apparatus and a medical image display apparatus according to another embodiment is explained with reference to FIG. 9. Functional units shown in FIG. 9 same as those shown in FIGS. 1 and 7 are denoted by the same reference numerals and signs, the above explanation is cited, and explanation of the functional units is omitted.

Medical image display apparatuses 13 and 14 according to this embodiment are respectively obtained by separating the functions of the condition setting unit 50 and the diagnostic image forming unit 60 in the image processing unit 47 shown in FIG. 2 and separately connecting the functions on the network W.

The communication unit 48 of the medical image display apparatus 13 also has the function of the model image acquiring unit 51 that acquires the data of the three-dimensional model image M accumulated in the accumulating unit 43 and a function of transmitted calculated correlation parameters to the accumulating unit 43.

The communication unit 48 of the medical image display apparatus 14 also has the function of the volume data acquiring unit 61, the function of the receiving unit 66 that receives the correlation parameters accumulated in the accumulating unit 43, and a function of transmitting a generated observation sectional image to the accumulating unit 43.

Two or more modalities (in the figure, an X-ray CT apparatus and an MRI apparatus) having different imaging systems are connected to the network W. The function of the condition setting unit 50 or the diagnostic image forming unit 60 is included in the data operating units 40 of these modalities in some case but both the functions are not included therein in other cases. When one of the functions is included in the modalities, the other function is included in the medical image display apparatuses 13 and 14 on the network W.

In this way, the data operating units 40 of the medical image diagnostic apparatuses and the medical image display apparatuses 13 and 14 are established on an information network system in a hospital.

Therefore, it is possible to adopt another modality that images the three-dimensional model image M (FIG. 3) instead of a modality that images volume data. This makes it possible to display plural observation sectional images at the same position from plural volume data imaged by various modalities.

Further, a browser terminal 15 not including the functions of the condition setting unit 50 and the diagnostic image forming unit 60 and used to simply display and observe an observation sectional image of the object P is connected to the network W.

In this way, the browser 15 is further connected to the information network system in the hospital. Therefore, a large volume of three-dimensional image data is rarely sent and received through the network W and congestion on the network W is reduced.

Figure 10:
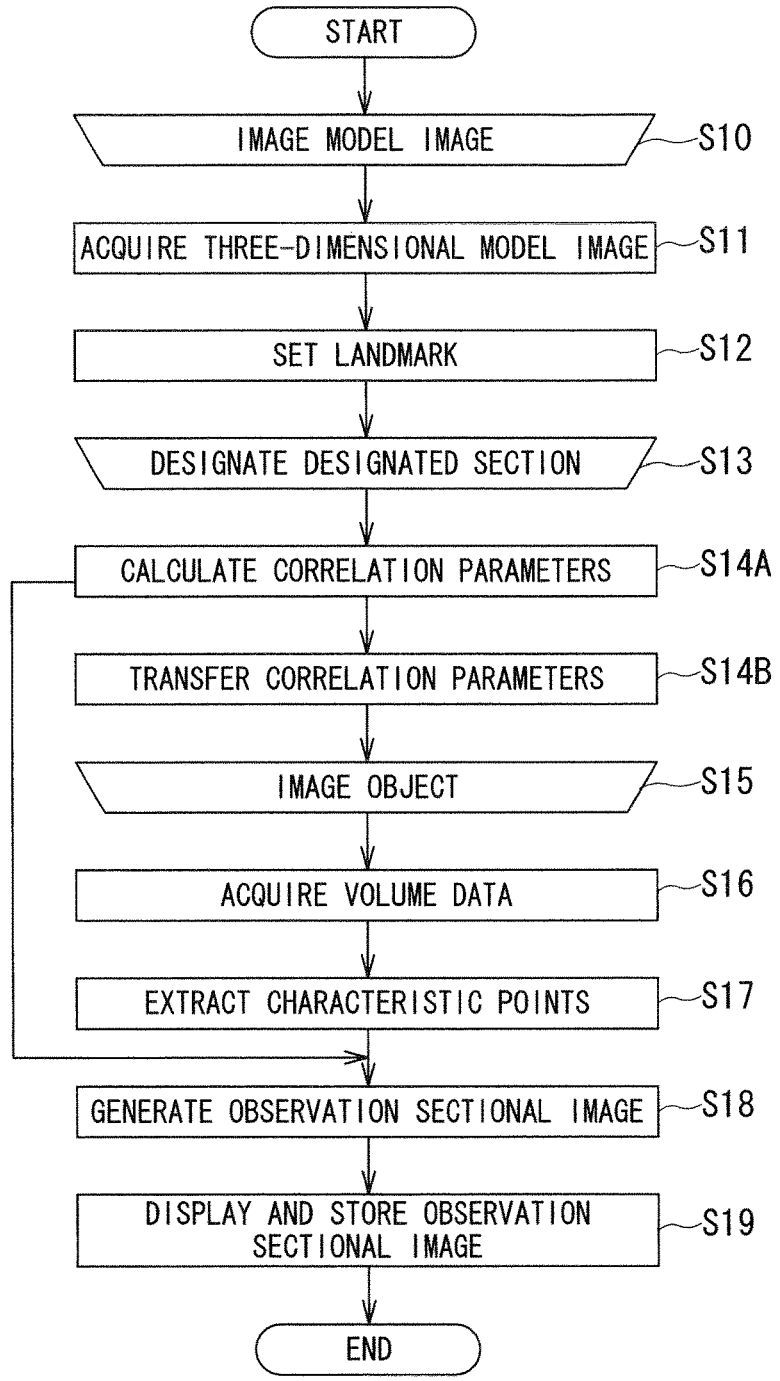
FIG. 10 is a flowchart for explaining the operation of the medical image diagnostic apparatus and the medical image display apparatus according to the embodiment.

The operation of the medical image diagnostic apparatus and the medical image display apparatus according to this embodiment is explained with reference to a flowchart of FIG. 10. Operation steps shown in FIG. 10 same as those shown in FIG. 5 are denoted by the same reference signs, the above explanation is cited, and explanation of the operation steps is omitted.

A procedure for observing a two-dimensional observation sectional image from volume data acquired by an MRI apparatus using image data acquired by an X-ray CT apparatus as a three-dimensional model image is explained. These operations are illustrated as being executed by the medical image display apparatuses 13 and 14 and the browser 15 on the network W separated from the modalities.

First, a three-dimensional model image needs to be imaged by the X-ray CT apparatus (S10). In this case, an image is not generated for the purpose of obtaining a three-dimensional model image. An image generated for other medical diagnosis is mainly diverted as a three-dimensional image.

First, an operator acquires a three-dimensional model image in the medical image display apparatus 13 directly from the X-ray CT apparatus or indirectly from the accumulating unit 43 (S11). The operator sets a landmark of the three-dimensional model image (S12) and designates the designated section N (S13). The medical image display apparatus 13 calculates correlation parameters (S14A) and transfers a result of the calculation to the accumulating unit 43 (S14B).

When the object P is imaged in the MRI apparatus (S15), volume data of the object P is acquired in the medical image display apparatus 14 (S16), characteristic points of the volume data are extracted (S17), the correlation parameters are acquired from the accumulating unit 43, and an observation sectional image is generated (S18). The generated observation sectional image is stored in the accumulating unit 43. The operator can display the observation sectional image on the display unit 42 by accessing the observation sectional image from the browser 15 (S19).

In this way, image data after imaging is processed in the medical image display apparatuses 13 and 14 on the network W separated from the modalities. This makes it possible to reduce time in which a patient is tied down and improve an operating ratio of the modalities.

The generated observation sectional image can be viewed on the browser 15, which is a general-purpose product. Therefore, it is possible to also improve processing efficiency of the medical image display apparatuses 13 and 14.

With the medical image display apparatus explained with reference to FIGS. 7 to 10, designation of the designated section N performed by using a three-dimensional model image can be performed in a terminal connected to a network rather than on the modalities.

When a reading terminal connected separately and independently from the modalities is present on the network, if an observation sectional image is created on the modalities, only an observation sectional image as two-dimensional image data is transferred to the reading terminal. Therefore, a transfer burden on the network is reduced.

It is possible to transfer all volume data and position information (correlation parameters, etc.) of an observation section from the modalities to the reading terminal and cause the reading terminal to generate a target observation sectional image. Consequently, since it is possible to cause the reading terminal to carry out generation processing for an observation sectional image. Therefore, a burden of data processing in the modalities is reduced.

The present invention is not limited to the embodiments explained above. The present invention can be modified as appropriate and carried out without departing from the scope of the common technical idea.

For example, in the embodiments, the head of the object P is illustrated as the imaging target. However, the present invention can also be applied to the internal organs, the blood vessels, and the skeleton portion other than the head. The MRI apparatus and the X-ray CT apparatus are illustrated as the modalities that image volume data. However, the modalities are not limited to these apparatuses.

The anatomical characteristic points are illustrated as the characteristic points respectively acquired and extracted from the three-dimensional model image and the volume data in the embodiments. However, the characteristic points are not limited to the anatomical characteristic data. For example, in various analysis modes using image contrasts proposed in the medical image analysis field, characteristic points in terms of luminance display of the analysis modes may be used.

In the embodiments, the three-dimensional model image is used to designate the designated section N. However, a two-dimensional model may be used. For example, in imaging of the head or the spine, section designation is often applied to a median section or a coronal section. In this case, a three-dimensional mode is not always necessary. It is possible to perform the section designation if one two-dimensional model is present.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical diagnostic imaging apparatus comprising:
    a magnetic resonance imaging (MRI) scanner or an X-ray CT imaging scanner configured to provide volume image data of a region-of-interest (ROI) of a first object within an apparatus coordinate system of the imaging scanner; and
    at least one computer configured to execute stored computer programs which
    (i) designate or retrieve landmark S in a model image or previously obtained volume image data of region corresponding to said ROI in said first object or a second object;
    (ii) designate any desired section of the model image or the previously obtained volume image data;
    (iii) calculate correlation parameters from the landmark S and said designated section, said landmark and correlation parameters defining an image coordinate system within said model image or previously obtained volume image data;
    (iv) acquire new volume image data of the region of interest in said first object;
    (v) extract at least one characteristic point in the acquired new volume image data corresponding to the previously designated an landmark S; and
    (vi) generate an observation section image, corresponding to said designated section, from the acquired new volume image data using (a) the extracted at least one characteristic point and (b) the previously calculated correlation parameters within said image coordinate system.

2. The medical diagnostic imaging apparatus according to claim 1, wherein the at least one computer is further configured to execute stored computer programs which reconstruct (a) the previously obtained volume image data from which the at least one characteristic point is extracted and (b) the new volume image data from which the observation sectional image is to be generated from the same object using image data generated by different imaging methods.

3. The medical diagnostic imaging apparatus according to claim 1, wherein the at least one computer is further configured to execute stored computer programs which generate said model image as a virtual image.

4. The medical diagnostic imaging apparatus according to claim 1, wherein said model image is generated by said at least one computer from volume image data of the same or different object.

5. The medical diagnostic imaging apparatus according to claim 1, wherein said model image is generated by said at least one computer using the same or a different modality.

6. The medical diagnostic apparatus according to claim 1, wherein the at least one computer is further configured to execute stored computer programs which extract said at least one characteristic point as at least one anatomical characteristic point in (a) the new volume image data or (b) at least one luminance characteristic point on a display.

7. The medical diagnostic imaging apparatus according to claim 1, wherein at least one computer is further configured to execute stored computer programs which set an imaging condition to prevent resolution of the observation sectional image from changing depending on sectional direction.

8. The medical diagnostic imaging apparatus according to claim 1, wherein:
    the correlation parameters are stored in association with character data, and
    the at least one computer of the medical diagnostic imaging apparatus is further configured to designate the character data and thereby cause generation of the observation sectional image.

* * * * *